United States Patent [19]

Hoffmann et al.

[11] 4,197,411
[45] Apr. 8, 1980

[54] BICYCLIC ALDEHYDES

[75] Inventors: Werner Hoffmann, Neuhofen; Karl von Fraunberg, Bobenheim, both of Fed. Rep. of Germany

[73] Assignee: BASF Aktiengesellschaft, Fed. Rep. of Germany

[21] Appl. No.: 898,036

[22] Filed: Apr. 20, 1978

[30] Foreign Application Priority Data

May 4, 1977 [DE] Fed. Rep. of Germany ....... 2719976

[51] Int. Cl.$^2$ ..................... C07C 47/34; C07C 47/44; C07C 69/02
[52] U.S. Cl. .................................. 560/256; 568/820; 260/648 R; 260/601 H; 260/598; 260/410.5
[58] Field of Search ............................ 260/598, 410.5; 560/256

[56] References Cited

U.S. PATENT DOCUMENTS 3,067,244  12/1962  Robinson et al. ................... 562/510

FOREIGN PATENT DOCUMENTS 1350741  12/1963  France ..................................... 260/598
49-25668  7/1974  Japan ..................................... 560/120

OTHER PUBLICATIONS

Brieger, Tetrahedron Letters, No. 28 (1963) 1949–1951.
Ohloff, "Fortschritte der Chemischen Forschung" 12 (1969) 212–215.
Saver, Angewandte Chemie, 79 (1967) 76–94.
Duttmann et al., Ann. Chem. (1976) 1753–1756.

*Primary Examiner*—Bernard Helfin
*Attorney, Agent, or Firm*—Keil & Witherspoon

[57] ABSTRACT

2-Halomethyl-, 2-alkoxymethyl- and 2-acyloxymethyl-3-methyl-3-formyl-bicyclo[2.2.1]heptane and -hept-5-ene and a process for their preparation.

The new compounds are obtained by reacting cyclopentadiene or dicyclopentadiene with the corresponding 4-halo-, 4-alkoxy- or 4-acyloxy-2-methyl-crotonaldehydes under the conventional conditions for Diels-Alder reactions, with or without subsequent catalytic hydrogenation of the Diels-Alder adduct obtained. The new compounds provide an industrially easily realized and advantageous method of synthesis of the sought-after essential ingredients of natural sandalwood oils.

6 Claims, No Drawings

BICYCLIC ALDEHYDES

The present invention relates to 2-halomethyl-, 2-alkoxymethyl-and 2-acyloxymethyl-3-methyl-3-formyl-bicyclo[2.2.1]heptane and the corresponding hept-5enes and to a process for their preparation by a Diels-Alder reaction of cyclopentadiene with the corresponding 4-halo-, 4-alkoxy- or 4-acyloxy-2-methyl-crotonaldehydes, optionally followed by hydrogenation.

Accordingly, the invention relates to new bicyclic aldehydes of the general formula I

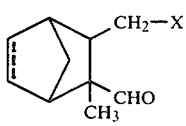

where X is Cl, Br, —OR or —O—CO—R, R is a saturated hydrocarbon radical of 1 to 10, preferably of 1 to 4, carbon atoms and the broken line may represent an additional C—C bond.

The invention further relates to a process for the preparation of the bicyclic aldehydes of the general formula I

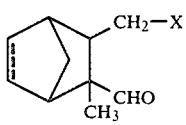

where X and the broken line have the above meaning, wherein cyclopentadiene or dicyclopentadiene is reacted with an α, β-unsaturated aldehyde of the general formula II

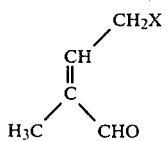

where X has the above meaning, under the conventional conditions for Diels-Alder reactions, after which the resulting Diels-Alder adduct may or may not be hydrogenated catalytically.

The new compounds are industrially particularly important since on the one hand they can be prepared in a simple manner, and with very good yields, from industrially readily accessible starting compounds, whilst on the other hand they provide an industrially relatively easily realized and advantageous method of synthesis of the sought-after essential ingredients of natural sandalwood oils, namely α- and β-santalene and α- and β-santalol.

Tetrahedron Letters 1963, page 1949 discloses a process for the preparation of β-santalene in which the key step is the Diels-Alder reaction of cyclopentadiene with geraniol. However, this process is industrially unacceptable since the Diels-Alder reaction only takes place with a yield of 4% and furthermore it is rather difficult to separate the desired Diels-Alder adduct from concomitant compounds.

Attempts to react geranic acid derivatives or citral with cyclopentadiene by a Diels-Alder reaction, along the lines of a β-santalene synthesis, have only given minimal yields of the Diels-Alder adduct, and this is attributed to steric hindrance by the trisubstituted or tetrasubstituted C=C group (cf. Ann. Chem. 1976, pages 1753–56).

In contrast, the Diels-Alder reaction in the process of the invention gives yields of from 60 to 95% of theory. β-Santalol can then be prepared from the compounds of the invention, for example by the method of synthesis schematically represented below, in a few industrially easily realized reaction steps.

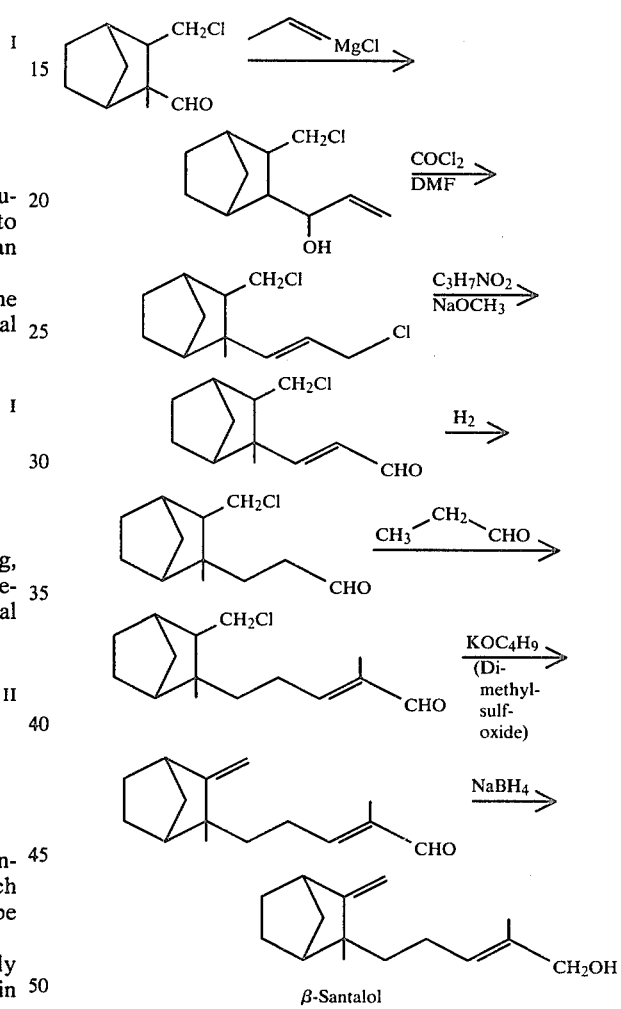

β-Santalol

Cyclopentadiene, required as the starting compound for the process of the invention, is commercially and cheaply available in the form of its dimer, dicyclopentadiene. Cyclopentadiene can be obtained from dicyclopentadiene by thermal depolymerization and distillation. However, if the Diels-Alder reaction is carried out thermally, dicyclopentadiene can be employed as such, since it is necessarily depolymerized at the prevailing reaction temperature.

Amongst the compounds II, the compound where X is —O—Ac, i.e. β-formylcrotyl acetate, which is an intermediate of an industrial method of synthesizing vitamin A, is very advantageously obtainable from acetone by hydroformylation, subsequent vinylation, methylation, allyl rearrangement and acetal cleavage. Compounds of the formula II, where X is a higher acyloxy radical, can readily be obtained from β-formylcrotyl acetate by transesterification. The halides of the formula II can be obtained in a simple manner from vinylmethylglyoxaldimethylacetal by rearrangement with HCl, HBr or phosgene, in accordance with the following equation:

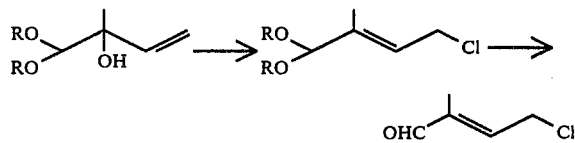

Essentially, two methods of carrying out the Diels-Alder reaction are known, i.e. a thermal method and a catalytic method.

When the reaction is carried out by the thermal method, a mixture of cyclopentadiene or dicyclopentadiene with the dienophil of the formula II, with or without an inert solvent, is heated, for the duration of the reaction, at from 100° to 250° C., preferably from 140 to 180° C. The reaction generally requires from 1 to 20 hours, preferably from 3 to 10 hours, depending on the nature of the dienophil. In general, the cyclopentadiene and the compound of the formula II are used in a molar ratio of from 1:1 to 3:1; if dicyclopentadiene is used, from 0.5 to 1.5 moles per mole of compound II in general suffice.

To avoid possible resinification, a small amount, i.e. from about 10 to 100 mg per mole of cyclopentadiene or dicyclopentadiene, of a stabilizer conventionally used in Diels-Alder reactions, e.g. hydroquinone, is generally added to the reaction mixture.

The reaction can be carried out in the absence of solvents or in an inert solvent.

Examples of suitable inert solvents are aliphatic hydrocarbons, e.g. pentane, hexane, cyclohexane and hydrocarbon fractions; aromatic hydrocarbons, e.g. benzene, toluene and xylene; chlorohydrocarbons, e.g. methylene chloride, chloroform and chlorobenzene; ethers, e.g. diethyl ether, dipropyl ether, diisopropyl ether, tetrahydrofuran and anisole, alcohols, e.g. methanol, ethanol, propanol, isopropanol and cyclohexanol; ketones, e.g. acetone, methyl ethyl ketone and methyl isopropyl ketone; amides, e.g. dimethylformamide, dimethylacetamide and hexamethylphosphorotriamide; nitro compounds, e.g. nitromethane and nitrobenzene; and mixtures of the above solvents.

The reaction may be carried out either under atmospheric pressure or under the autogenous pressure of the reactants, in a closed reaction vessel.

The reaction mixture may be worked up in the conventional manner, for example by distillation.

For further details of the Diels-Alder reaction, reference may be made to R. Sauer, Angew. Chem. 79 (1967), 77–94.

The reaction can be carried out particularly advantageously by the catalytic method. Suitable catalysts are Lewis acids, e.g. boron fluoride etherate, aluminum trichloride, iron -(III) chloride, zinc chloride, tin-(IV) chloride, titanium-(IV) chloride and antimony-(V) chloride. To carry out the catalytic reaction, the procedure described above is essentially followed, but at a lower temperature, i.e. at from −50° to +100° C., preferably from −20° to +30° C. Because of the lower reaction temperature it is generally necessary to depolymerize dicyclopentadiene to cyclopentadiene before carrying out the reaction. The reaction time is generally from 30 minutes to 20 hours, especially from 1 to 5 hours.

The amount of catalyst is generally from 0.01 to 5% by weight, preferably from 0.1 to 2% by weight, based on the employed compound of the formula II. The molar ratio of cyclopentadiene to the α, β-unsaturated aldehyde of the formula II is preferably from 1:1 to 1.2:1 if the catalytic method is used. Suitable solvents are those mentioned in connection with the thermal method.

Both embodiments of the process can be carried out either batchwise or continuously.

To hydrogenate the Diels-Alder adduct to give the compound I, it is advantageous to employ the adduct (if appropriate after gently removing the solvent) without further purification, since there is the danger of a retro-Diels-Alder reaction during distillation of the adduct.

To carry out the hydrogenation, the Diels-Alder adduct may or may not be dissolved in a suitable solvent, e.g. ethyl acetate, methanol or methylene chloride; the hydrogenation catalyst is added and the hydrogenation is carried out in a conventional manner. Suitable catalysts are noble metals, e.g. platinum, palladium, rhodium and ruthenium, on carriers, e.g. charcoal, alumina, silica gel, calcium carbonate and the like. Neither the reaction temperature nor the pressure is critical; they may be, respectively, from room temperature to 100° C., and from atmospheric pressure to 300 bars hydrogen pressure. For working up, the catalyst is separated off, and the reaction product I is isolated by fractional distillation. For further details of such a catalytic hydrogenation of a double bond, reference may be made to G. Schiller in Houben-Weyl, volume IV/2, pages 248–303 (1955), and K. Wimmer in Houben-Weyl, volume IV/2, pages 143–152 and 163–192.

The compounds of the invention provide an industrially relatively easily implemented and advantageous method of synthesis of sought-after essential ingredients of natural sandalwood oils.

EXAMPLE 1

(a)

2-Chloromethyl-3-methyl-3-formyl-bicyclo[2.2.1]hept-5-ene 5 ml of boron fluoride etherate were added to 1 liter of methylene chloride and the mixture was cooled to −20° C. A solution of 452 g (6.84 moles) of cyclopentadiene and 712 g (6.0 moles) of 3-formyl-crotyl chloride were added, whilst stirring, at a rate such that the reaction temperature did not rise above −10° C. The reaction mixture was then stirred for 3 hours at −10° C. To work up the reaction mixture, it was poured onto 1 kg of ice and neutralized with sodium carbonate solution, and the methylene chloride solution was washed neutral with water. After distilling off the solvent under reduced pressure (12 mm Hg/50° C.), 1,139 g of reaction product remained. A sample distillation showed that the yield was about 90% of theory.

Boiling point 69° C./0.08 mm Hg; $n_D^{25} = 1.5074$

IR spectrum: 2,960, 2,875, 2,800, 2,700, 1,720, 1,450, 1,330, 1,270, 905, 740 and 710 cm$^{-1}$ NMR spectrum (60 Mc/s, CDCl$_3$): 0.95 s (CH$_3$), 1.35 m (2H), 2.7–3.3 m (5H), 6.25 m (2H) and 9.55 s (1H).

(b) 2-Chloromethyl-3-methyl-3-formyl-bicyclo[2.2.1]heptane

The reaction product obtained as described in 1 (a) was taken up in 800 ml of ethyl acetate, 5 g of 5% strength palladium on charcoal were added to the solution and the hydrogenation was carried out at room temperature under a hydrogen pressure of 5 bars until no further hydrogen was taken up. The catalyst was then filtered off and the solvent was removed under reduced pressure (12 mm Hg/50° C.). The reaction product which remained was subjected to fractional distillation, giving 915 g of 2-chloromethyl-3-methyl-3-formyl-bicyclo 2.2.1 heptane (yield: 82%).

Boiling point 64°-65° C./0.05 mm Hg; $n_D^{25} = 1.5022$

IR spectrum: 2.960, 2,880, 2,800, 2,700, 1,720, 1,460 and 735 cm$^{-1}$

NMR spectrum (100 Mc/s, CDCl$_3$): 1.05 s (CH$_3$), 1.1–1.7 m (7H), 2.27 m (1H), 2.43 m (1H), 2.6 m (1H), 2.5 d (2H) and 9.4 s (1H).

It was established, by using shifting agents, that the product was probably the endo-compound (E-FOD series).

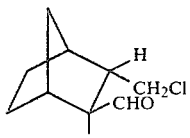

EXAMPLE 2

(a) 2-Acetoxymethyl-3-methyl-3-formyl-bicyclo[2.2.1-]hept-5-ene 5 ml of boron fluoride etherate were added to 400 ml of methylene chloride and the mixture was cooled to −15° C. A solution of 132 g (2 moles) of freshly distilled cyclopentadiene and 256 g (1.8 moles) of 3-formylcrotyl acetate was added dropwise, whilst stirring, at a rate such that the reaction temperature did not rise above −10° C. The reaction was then allowed to continue for 2 hours at −10° C., whilst stirring. For working up, about 0.5 kg of ice was added, the mixture was neutralized with sodium bicarbonate solution, the aqueous phase was separated off and the methylene chloride was removed under reduced pressure (12 mm Hg/50° C.). The reaction product which remained was subjected to fractional distillation, giving 337 g of main fraction (yield: 90%).

Boiling point 83–84° C./0.02 mm Hg; $n_D^{25} = 1.4862$

IR spectrum: 2,960, 2,870, 2,810, 2,700, 1,730, 1,715, 1,450, 1,360, 1,230 and 1,030 cm$^{-1}$ NMR spectrum (60 Mc/s, CDCl$_3$): 0.9 s (CH$_3$), 1.3 m (2H), 1.9 s (CH$_3$), 2.5–2.9 m (3H), 3.7 d and 4.0 m (2H), 6.2 m (2H) and 9.5 s (1H).

(b) 2-Acetoxymethyl-3-methyl-3-formyl-bicyclo[2.2.1]heptane 330 g (1.58 moles) of 2-acetoxymethyl-3-methyl-3-formyl -bicyclo[2.2.1]hept-5-ene, obtained as described in 2(a), were dissolved in 500 ml of ethyl acetate, 3 g of a 5% strength palladium/charcoal catalyst were added to the solution, and hydrogenation was carried out at from 25° to 35° C. at 5 bars hydrogen pressure until no further hydrogen was taken up. The catalyst was then filtered off and the ethyl acetate was removed under reduced pressure (12 mm Hg/50° C.). On fractional distillation of the reaction product, 317 g of main fraction (yield: 94%) were obtained.

Boiling point 91° C./0.01 mm Hg; $n_D^{25} = 1.4791$

IR spectrum: 2,950, 2,870, 2,700, 1,735, 1,720, 1,450, 1,360, 1,230 and 1,030 cm$^{-1}$.

NMR spectrum: 0.95 s (CH$_3$), 1.0–1.6 m (7H), 2.2 m (2H), 4.0 m (2H) and 9.3 s (1H).

EXAMPLE 3

2-Acetoxymethyl-3-methyl-3-formyl-bicyclo[2.2.1-]hept5-ene 66 g (1 mole) of freshly distilled cyclopentadiene, 71 g (0.5 mole) of 3-formyl-crotyl acetate and 1 g of hydroquinone were heated for 10 hours at 160° C. under nitrogen in a 1 liter stirred autoclave. The reaction mixture was then subjected to fractional distillation, given 65 g of the product (yield: 62%).

Boiling point 89°–90° C./0.05 mm Hg; $n_D^{25} = 1.4865$

EXAMPLE 4

2-Acetoxymethyl-3-methyl-3-formyl-bicyclo[2.2.1-]hept-5-ene 264 g (2 moles) of dicyclopentadiene, 284 g (2 moles) of 3-formyl-crotyl acetate and 5 g of hydroquinone were heated for 10 hours at 160° C. under a N$_2$ atmosphere in a 1-liter stirred autoclave. The reaction mixture was then distilled through a column, giving 275 g (yield: 64% of theory) of the product.

We claim:

1. A bicyclic aldehyde of the general formula I

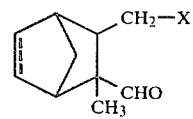

where X is Cl, Br, —OR or —O—CO—R, R is a saturated hydrocarbon radical of 1 to 10 carbon atoms and the broken line may represent an additional C—C bond.

2. A bicyclic aldehyde as claimed in claim 1, wherein R is alkyl of 1 to 4 carbon atoms.

3. 2-Chloromethyl-3-methyl-3-formyl-bicyclo[2.2.1-]hept -5-ene.

4. 2-Chloromethyl-3-methyl- 3-formyl-bicyclo[2.2.1-]heptane.

5. 2-Acetoxymethyl-3-methyl-3-formyl-bicyclo[2.2.1-]hept- 5-ene.

6. 2-Acetoxymethyl-3-methyl-3-formyl-bicyclo[2.2.1]-heptane.

* * * * *